United States Patent [19]

Iwakuma et al.

[11] Patent Number: 4,975,460

[45] Date of Patent: Dec. 4, 1990

[54] INDANOXYACETIC ACID DERIVATIVES

[75] Inventors: Takeo Iwakuma, Ageo; Harumichi Kohno, Koganei; Yasuhiko Sasaki; Katsuo Ikezawa, both of Urawa; Akio Odawara, Tokyo, all of Japan

[73] Assignee: Tanabe Seiyaku Co., Ltd., Osaka, Japan

[21] Appl. No.: 311,854

[22] Filed: Feb. 17, 1989

[30] Foreign Application Priority Data

Feb. 26, 1988 [JP] Japan .................. 63-45704

[51] Int. Cl.$^5$ .................. A61K 31/215; A61K 31/19; C07C 317/12

[52] U.S. Cl. .................. 514/510; 514/538; 514/541; 514/562; 560/10; 560/12; 560/13; 562/428

[58] Field of Search .................. 560/10, 12, 13; 562/428; 514/542, 562, 538, 510, 541

[56] References Cited

U.S. PATENT DOCUMENTS 4,820,705  4/1989  Nickl et al. .................. 514/247

FOREIGN PATENT DOCUMENTS 63-23853  2/1988  Japan .

*Primary Examiner*—Werren B. Lone
*Assistant Examiner*—Vera C. Clarke
*Attorney, Agent, or Firm*—Birch, Stewart, Kolasch, & Birch

[57] ABSTRACT

Novel indanoxyacetic acid derivatives of the formula:

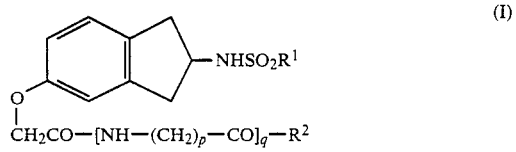

wherein $R^1$ is a lower alkyl group, a substituted or unsubstituted phenyl group, naphtyl group or a sulfur-containing heterocyclic group, $R^2$ is hydroxy group or a protected hydroxy group, p is an integer of 2 or 3, and q is an integer of 0 or 1, and a salt thereof are disclosed.

Said derivative (I) and a salt thereof are useful as a platelet aggregation-inhibiting agent and an agent for the treatment, amelioration and/or prophylaxis of a variety of thrombosis, embolism, coronary and cerebral vascular smooth muscl vellication, asthma, and the like.

5 Claims, No Drawings

INDANOXYACETIC ACID DERIVATIVES

This invention relates to novel indanoxyacetic acid derivatives and processes for preparing the same.

It is known that Thromboxan $A_2$ (hereinafter, simply referred to as "$TxA_2$") is a metabolite of arachidonic acid which exists widely in various organs of animals (e.g., liver, kidney, lung, brain, etc.) and that the $TxA_2$ having platelet aggregation activity induces a variety of thrombosis such as peripheral vascular thrombosis, pulmonary embolism, coronary artery thrombosis, myocardial infarction, transient ischemia, and like. As an agent for inhibiting the platelet aggregation caused by $TxA_2$, there is known 4-(2-benezenesulfonylaminoethyl)phenoxyacetic acid [cf. Thrombosis Research, 35, 379–395, (1984)].

As a result of various investigations, we have now found that novel indanoxyacetic acid derivatives which show stronger $TxA_2$ antagonistic activity as compared with known compound.

Namely, this invention relates to an indanoxyacetic acid derivative of the formula:

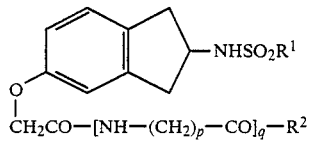
(I)

wherein $R^1$ is a lower alkyl group, a substituted or unsubstituted phenyl group, naphtyl group or a sulfur-containing heterocyclic group, $R^2$ is hydroxy group or a protected hydroxy group, p is an integer of 2 or 3, and q is an integer of 0 or 1, or a salt thereof.

The indanoxyacetic acid derivatives (I) of the present invention show potent $TxA_2$ antagonistic activity and are useful as a platelet aggregation inhibiting agent and as an agent for the treatment, amelioration and/or prophylaxis of thrombotic diseases (e.g., thrombosis, embolism, coronary and cerebral vascular smooth muscle vellication, asthma).

Examples of the compound of the present invention are those of the formula (I) in which $R^1$ is a lower alkyl group (e.g., methyl, ethyl, propyl, butyl, pentyl, hexyl), phenyl group, a phenyl group substituted with a group selected from a lower alkyl group (e.g., methyl, ethyl, propyl, butyl, pentyl, hexyl) and a halogen atom (e.g., chlorine atom, bromine atom, iodine atom), naphtyl group or a sulfur-containing heterocyclic group (e.g., thienyl), $R^2$ is hydroxy group, a lower alkoxy group (e.g., methoxy, ethoxy, propoxy, butoxy), a substituted or unsubstituted phenyl-lower alkyl group (e.g., benzyloxy, p-methoxybenzyloxy, p-nitrobenzyloxy) or benzhydryloxy group, p is 2 or 3 and q is 0 or 1.

Among these compounds of the present invention, preferred examples include those of the formula (I) in which $R^1$ is a $C_{1-4}$alkyl group, phenyl group, a halogenophenyl group, a lower alkyl-phenyl group, naphtyl group or thienyl group, and $R^2$ is hydroxy group or a $C_{1-4}$alkoxy group.

More preferred examples are those of the formula (I) in which $R^1$ is phenyl group, chlorophenyl group, methylphenyl group and $R^2$ is hydroxy group or methoxy group.

Other preferred examples are those of the formula (I) in which q is 1.

The compound (I) of the present invention may exist in the form of two optically active isomers due to one asymmetric carbon atom, and the invention includes these optically active isomers and a mixture thereof.

According to the present invention, the compound (I) can be prepared by the step or steps of:

(A) condensing a compound of the formula:

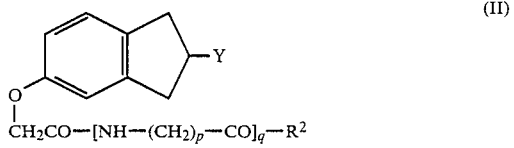
(II)

wherein Y is amino group or a reactive residue, and $R^2$, p and q are the same as defined above, or a salt thereof with a sulfonyl compound of the formula:

$$R^1SO_2X^1 \qquad (III)$$

wherein $R^1$ is the same as defined above, and (a) $X^1$ is hydroxy group or a reactive residue when Y is amino group or
(b) $X^1$ is amino group when Y is a reactive residue; or (B) condensing a compound of the formula:

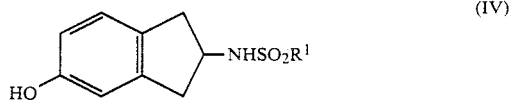
(IV)

wherein $R^1$ is the same as defined above with a compound of the formula:

$$X^2CH_2CO-[NH-(CH_2)_p-CO]_q-R^2 \qquad (V)$$

wherein $X^2$ is a reactive residue, and $R^2$, p and q are the same as defined above.

The compound (I) in which q is 1, i.e., a compound of the formula:

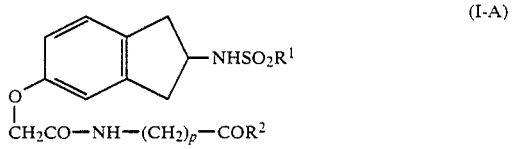
(I-A)

wherein $R^1$, $R^2$ and p are the same as defined above, can be prepared by:

(C) condensing a compound of the formula:

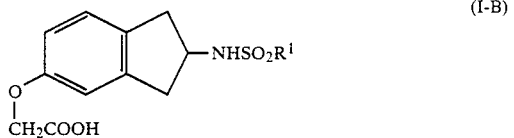
(I-B)

wherein $R^1$ is the same as defined above, or a reactive derivative thereof with a compound of the formula:

$$NH_2-(CH_2)_p-COR^2 \qquad (VI)$$

wherein $R^2$ and p are the same as defined above.

Further, the compound (I) in which $R^2$ is hydroxy group, i.e., a compound of the formula:

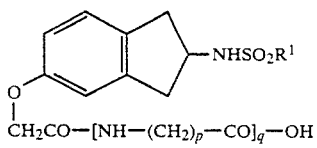

(I-C)

wherein $R^1$, p and q are the same as defined above, can be prepared by:

(D) removing a protecting group from a compound of the formula:

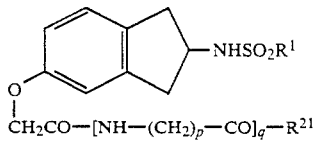

(I-D)

wherein $R^{21}$ is a protected hydroxy group, and $R^1$, p and q are the same as defined above.

Any protecting group, which is removable, for example, by a conventional manner such as hydrolysis, acid-treatment and reduction, can be used to protect the hydroxy group of the starting compounds (II), (V) and (VI). Examples of such protecting group of hydroxy group include a lower alkyl group such as methyl group, ethyl group, propyl group or butyl group, a substituted or unsubstituted phenyl-lower alkyl group such as benzyl group, p-methoxybenzyl group, p-nitrobenzyl group or benzhydryl group.

The condensation of the compound (II) or a salt thereof (e.g., inorganic acid addition salts such as hydrochloride, hydrobromide, hydroiodide, sulfate or nitrate, or organic acid addition salts such as maleate, fumarate, acetate, oxalate, succinate or p-toluenesulfonate) with the sulfonyl compound (III) can be carried out in the presence or absence of an acid acceptor in a solvent. Examples of the reactive residue (Y or $X^1$) of the compound (II) or (III) include a halogen atom such as chlorine atom, bromine atom or iodine atom, a lower alkylsulfonyl group such as methanesulfonyl group, a substituted or unsubstituted phenylsulfonyl group such as benzenesulfonyl group or p-toluenesufonyl group. Examples of the acid acceptor include inorganic bases such as alkali metal carbonates (e.g., sodium carbonate, potassium carbonate) or alkali metal bicarbonates (e.g., sodium bicarbonate, potassium bicarbonate), and organic bases such as trialkylamines (e.g., triethylamine, trimethylamine) or pyridine. Water, ethyl acetate, toluene, benzene, chloroform, methylene chloride, tetrahydrofuran and a mixture thereof are suitable as the solvent. It is preferred to carry out the reaction at a temperature of $-10°$ to $100°$ C., especially $-10°$ to $50°$ C.

The condensation of the compound (IV) with the acetic acid compound (V) can be carried out in the presence of an acid acceptor in an inactive solvent (e.g., acetone, chloroform, lower alkanols such as methanol or ethanol, methylene chloride, tetrahydrofuran, dimethylsulfoxide, dimethylformamide or a mixture thereof). Examples of the acid acceptor include inorganic bases such as alkali metal carbonates (e.g., sodium carbonate, potassium carbonate), alkali metal bicarbonates (e.g., sodium bicarbonate, potassium bicarbonate) or alkali metal oxides (e.g., sodium oxide, potassium oxide), and organic bases (e.g., trimethylamine, triethylamine, pyridine). It is preferred to carry out the reaction at a temperature of $0°$ to $100°$ C., especially $20°$ to $100°$ C.

The condensation of the carboxylic acid compound (I-B) or a reactive derivative at the carboxyl group thereof with the amino acid compound (VI) can be carried out in a conventional manner of peptide synthesis. For example, the condensation of the compound (I-B) in the form of a free carboxylic acid with the compound (VI) can be carried out in the presence of a condensing agent in a solvent. Examples of the condensing agent include carbonyldiimidazole, dicyclohexylcarbodiimide and the like. Tetrahydrofuran, methylene chloride, chloroform, toluene and benzene are suitable as the solvent. It is preferred to carry out the reaction at a temperature of $-10°$ to $100°$ C., especially $0°$ to $60°$ C. On the other hand, the condensation of the reactive derivative of the compound (I-B) with the compound (VI) can be carried out in the presence or absence of an acid acceptor. Examples of the reactive derivative of the compound (I-B) include the corresponding acid halides thereof (e.g., acid chlodride, acid bromide), mixed anhydrides (e.g., a mixed anhydride with alkyl carbonates) and active esters thereof (e.g., ester with pentachlorophenol, p-nitrophenol, 2,4,6-trinitrophenol, N-hydroxysuccinimide). Examples of the acid acceptor include alkali metal carbonates (e.g., sodium carbonate, potassium carbonate), alkali metal bicarbonates (e.g., sodium bicarbonate, potassium bicarbonate), alkali metal oxides (e.g., sodium oxide, potassium oxide), organic amines (e.g., triethylamine) and pyridine. It is preferred to carry out the reaction in a solvent (e.g., tetrahydrofuran, methylene chloride) at a temperature of $-10°$ to $100°$ C., especially $0°$ to $50°$ C.

The removal of the protecting group from the compound (I-D) may be conducted in a conventional manner such as hydrolysis or catalytic reduction. For example, when $R^{21}$ of the compound (I-D) is a hydroxy group protected with a lower alkyl group, the removal of said protecting group can be carried out by treating said compound with an alkali agent or an acid in a solvent. Examples of the alkali agent include alkali metal hydroxides (e.g., sodium hydroxide, potassium hydroxide). Examples of the acids include mineral acids (e.g., hydrochloric acid, hydrobromic acid). Water or lower alkanols (e.g., methanol, ethanol, propanol) are suitable as the solvent. Moreover, when $R^{21}$ is a hydroxy group protected with a substituted or unsubstituted phenyl-lower alkyl group, the removal of said protecting group can be conducted, for example, by treating said compound (I-D) with hydrogen gas in the presence of a catalyst (e.g., palladium-palladium carbonate, palladium carbon, palladium black) in a solvent (e.g., methanol, ethanol, tetrahydrofuran, ethyl acetate). It is preferred to carry out the reaction at a temperature of $10°$ to $100°$ C., especially $20°$ to $50°$ C.

All of the above-mentioned reactions of the present invention can be carried out without racemization, and hence, when optically active compounds are used as the starting materials, the desired compound (I) can be readily obtained in the optically active form.

The compound (I) can be used for pharmaceutical use either in the free form or in the form of a salt thereof. For the pharmaceutical use, the salt of the compounds is preferably pharmaceutically acceptable salts, for example, alkali metal salts (e.g., sodium salt or potassium salt), alkaline earth metal salts (e.g., calcium salt or magnesium salt), heavy metal salts (e.g., zinc salt), ammonium salt, organic amine salts (e.g., triethylamine salt, pyridine salt or ethanolamine salt), basic amino acid salts (e.g., lysine salt, arginine salt or histidine salt), and the like. These salts can be obtained by treating the compound (I) with stoichiometrically equimolar amount of the corresponding organic base or inorganic base.

The compound (I) or a salt thereof may be administered either orally or parenterally and may also be used in the form of a pharmaceutical preparation containing the same compound in admixture with pharmaceutical excipients suitable for oral or parenteral administration. The pharmaceutical preparations may be in solid form such as tablets, capsules or powders or in liquid form such as solutions, suspensions or emulsions. Moreover, when administered parenterally the pharmaceutical preparation may be in the form of injections.

The dose of the compound (I) or a salt thereof may vary over a wide range depending on the administration route, the age, body weight or conditions of patients and the kind and severity of diseases to be treated. In general, however, preferred daily dose of the compound (I) or a salt thereof is in range of 0.01 to 100 mg/kg/day, especially 0.1 to 50 mg/kg/day.

As mentioned hereinbefore, the compound (I) of the present invention or a salt thereof show potent TxA$_2$-antagonistic activity, and hence are useful as a platelet-aggregation inhibiting agent and and also useful for treatment, amelioration and/or prophylaxis of a variety of thrombosis or embolism such as cerebral thrombosis, coronary artery thrombosis, pulmonary thrombosis, pulmonary embolism, peripheral vascular embolism, thromboangiitis, and the like. Moreover, the compound (I) of the present invention or a salt thereof is also useful for the treatment, amelioration and/or prophylaxis of myocardial ischemia, unstable angina pectoris, coronary vellication, cerebral blood vessel vellication after subarachinoid hemorrhage, cerebral hemorrhage, asthma, and the like. Furthermore, although some known TxA$_2$-antagonists show excellent TxA$_2$-antagonistic activity but at the same time, show transient TxA$_2$-like activity, and hence have side effects such as platelet aggregation-inducing activity, bronchoconstriction-inducing activity or blood vessel constriction-inducing activity, the compound (I) of the present invention or salts thereof do not show such TxA$_2$-like activity when administered either orally or parenterally.

Concomitantly, the starting compound (II) of the present invention may be prepared, for example, by reacting a compound of the formula:

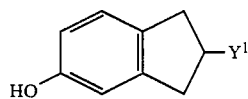

(VII)

wherein Y$^1$ is a protected amino group or a reactive residue, with an acetic acid derivative (V) (e.g., methyl bromoacetate) in the presence of an acid acceptor (e.g., potassium carbonate) in a solvent (e.g., acetone) and when Y$^1$ of the product is a protected amino group, removing the protecting group. Moreover, the starting compound (IV) may be prepared, for example, by reacting 2-amino-5-hydroxyindan with a sulfonyl compound of the formula: R$^1$SO$_2$Cl (wherein R$^1$ is the same as defined above) in the presence of an acid acceptor (e.g., alkali metal carbonates, organic amines) in a solvent (e.g., a mixture of chloroform and water).

Throughout the Specification and Claims, the terms "lower alkyl" and "lower alkoxy" should be interpreted as referring to alkyl having one to 6 carbon atoms and alkoxy having one to 6 carbon atoms, respectively.

The present invention will now be illustrated by the following examples of processes for preparing the new compounds according to the invention.

Experiment

Inhibiting effect on arachidonic acid-induced pulmonary embolism (in vivo):

A test compound dissolved in an aqueous CMC solution was orally administered to ddy-male mice fasted overnight. Three hours later, arachidonic acid (125 mg/kg) was injected to the tail of mice to induce pulmonary embolism, and recovery time (minutes) of locomotive activity of the mice (i.e., the duration from the injection of arachidonic acid to the time the mice recovered from respiratory distress and began to walk) was compared with that of a control group of mice to which an aqueous CMC solution was administered instead of the test compound solution. The inhibiting effect of each test compound on arachidonic acid-induced pulmonary embolism was estimated in terms of a minimum effective dose, i.e., the dose required to shorten the recovery time by at least 15% as compared with the control group.

The results are shown in the following Table 1.

TABLE 1

| Test Compounds (*) | Inhibiting effect on arachidonic acid-induced pulmonary embolism. Minimum Effective Dose (mg/kg) |
|---|---|
| (The compounds of the invention) | |
| Compound No. 1 | 0.03 |
| Compound No. 2 | 0.03 |
| Compound No. 3 | 0.3 |
| Compound No. 4 | 0.03 |
| Compound No. 5 | 0.03 |
| Compound No. 6 | 0.03 |
| Compound No. 7 | 0.1 |
| Known compound | 30 |

(*) note: Chemical name of each test compound:

Compound No.1: Sodium [2-(phenylsulfonylamino)indan-5-yl]oxyacetate
Compound No.2: Sodium {2-[(4-chlorophenyl)sulfonylamino]indan-5-yl}oxyacetate
Compound No.3: Sodium 3-{[2-(phenylsulfonylamino)indan-5-yl]oxyacetylamino}propionate
Compound No.4: Sodium 3-{[2-[(4-chlorophenyl)sulfonylamino]indan-5-yl]oxyacetylamino}propionate
Compound No.5: Sodium {2-[(2-naphtyl)sulfonylamino]indan-5-yl}oxyacetate
Compound No.6: Sodium {2-[(2-thienyl)sulfonylamino]indan-5-yl}oxyacetate
Compound No.7: Sodium {2-[(4-methylphenyl)sulfonylamino]indan-5-yl}oxyacetate
Known compound: 4-(2-benezenesulfonylaminoethyl)-phenoxyacetic acid (a compound disclosed in Thrombosis Research, 35, 379–395, 1984)

Example 1

(1) 2.71 g of methyl (2-aminoindan-5-yl)oxyacetate hydrochloride are added to a mixture of 80 ml of ethyl acetate, 40 ml of water and 415 mg of potassium carbonate and a solution of 2.11 g of 4-chlorophenylsulfonyl chloride in 40 ml of ethyl acetate is added dropwise thereto. The mixture is stirred for 2 hours and the ethyl acetate layer is separated. The ethyl acetate layer is washed successively with an aqueous 10% hydrochloric acid solution, an aqueous saturated sodium bicarbonate solution and an aqueous sodium chloride solution, dried and evaporated to remove solvent. 30 ml of methanol and 20 ml of 1N sodium hydroxide solution are added to the residue and the mixture is stirred at room temperature for 20 minutes. The reaction mixture is adjusted to pH 1 with an aqueous 10% hydrochloric acid solution and extracted with a mixture of chloroform and tetrahydrofuran. The extract is dried and evaporated to remove solvent. The residue is recrystallized from tetrahydrofuran-n-hexane-isopropyl ether to give 3.57 g of {2-[(4-chlorophenyl)sulfonylamino]indan-5-yl}oxyacetic acid as yellow prisms. Yield: 94% m.p. 170°–172° C.

MS(M/e): 381(M+)
IRV(Nujol)cm$^{-1}$: 3290, 1720
Sodium salt:
m.p. >250° C. (recrystallized from water-isopropanol)
MS(m/e): 404(M+ + 1), 426(M+ + Na), 448(M+ + 2Na-1)
IR$\nu$(Nujol)cm$^{-1}$: 3440, 3290

Examples 2–6

The corresponding starting compounds are treated in the same manner as described in Example 1 to give the compounds as shown in the following Table 1.

TABLE 1

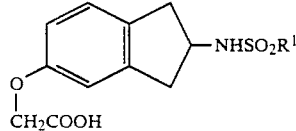
(I-a)

| Example Nos. | Compound (I-a) R$^1$ | Properties |
|---|---|---|
| 2 | phenyl | Yield: 95%<br>m.p. 154–156° C. (recrystallized from ethyl acetate-isopropyl ether-n-hexane)<br>MS(m/e): 347(M+)<br>IR$\nu$(Nujol)cm$^{-1}$: 1750, 3280<br>sodium salt<br>m.p. > 250° C. (recrystallized from water-isopropanol-isopropyl ether)<br>MS(m/e): 414(M+ + 2Na-1), 392(M+ + Na), 370(M+ + 1)<br>IR$\nu$(Nujol)cm$^{-1}$: 3270 |
| 3 | naphthyl | Yield: 94%<br>m.p. 149.5–151° C. (recrystallized from ethyl acetate-isopropyl ether-n-hexane)<br>MS(m/e): 397(M+)<br>IR$\nu$(Nujol)cm$^{-1}$: 3310, 3290, 1730<br>sodium salt<br>m.p. > 250° C. (recrystallized from water-isopropanol-isopropyl ether)<br>MS(m/e): 464(M+ + 2Na-1), 442(M+ + Na), 420(M+ + 1)<br>IR$\nu$(Nujol)cm$^{-1}$: 3290 |
| 4 | thienyl | Yield: 89%<br>m.p. 163–165° C. (recrystallized from ethyl acetate-isopropyl ether-n-hexane)<br>MS(m/e): 353(M+)<br>IR$\nu$(Nujol)cm$^{-1}$: 3300, 1710<br>sodium salt<br>m.p. > 250° C. (recrystallized from water-isopropanol-isopropyl ether)<br>MS(m/e): 420(M+ + 2Na-1), 398(M+ + Na), 376(M+ + 1)<br>IR$\nu$(Nujol)cm$^{-1}$: 3290 |
| 5 | 4-methylphenyl | Yield: 93%<br>m.p. 139–141° C. (recrystallized from ethyl acetate-n-hexane)<br>MS(m/e): 361(M+)<br>IR$\nu$(Nujol)cm$^{-1}$: 3290, 1705<br>sodium salt<br>MS(m/e): 428(M+ + 2Na-1), 406(M+ + Na), 384(M+ + 1)<br>IR$\nu$(Nujol)cm$^{-1}$: 3280 |

TABLE 1-continued (I-a)

[Structure: indane ring with —NHSO$_2$R$^1$ substituent and O—CH$_2$COOH substituent]

| Example Nos. | Compound (I-a) R$^1$ | Properties |
|---|---|---|
| 6 | —CH$_3$ | Yield: 84%<br>m.p. 174–176° C. (recrystallized from ethyl acetate-n-hexane)<br>MS(m/e): 285(M$^+$)<br>IR$\nu$(Nujol)cm$^{-1}$: 3290, 1720<br>sodium salt<br>MS(m/e): 352(M$^+$ + 2Na-1), 330(M$^+$ + Na), 308(M$^+$ + 1)<br>IR$\nu$(Nujol)cm$^{-1}$: 3230 |

Example 7

1.527 g of {2-[(4-chlorophenyl)sulfonylamino]indan-5-yl}oxyacetic acid are dissolved in a mixture of 15 ml of dichloromethane and 15 ml of tetrahydrofuran, and 3 ml of thionyl chloride are added to the solution. The mixture is refluxed under stirring for 2.5 hours. The reaction mixture is evaporated to remove solvent and the residue is dissolved in 30 ml of dichloromethane. The solution is added dropwise to a solution of 558 mg of methly 3-aminopropionate hydrochloride and 607 mg triethylamine in 15 ml of dichloromethane and the mixture is stirred overnight at room temperature. The reaction mixture is evaporated to remove solvent and the residue is extracted with ethyl acetate. The extract is washed with water, dried and evaporated to remove solvent. The residue is recrystallized from a mixture of tetrahydrofuranisopropyl ether-n-hexane to give 874 mg of methyl 3-{[2-[(4-chlorophenyl)sulfonylamino]indan-5-yl]oxyacetylamino}propionate as pale yellow prisms. Yield: 94% m.p. 126°–127.5° C.
MS(m/e): 466(M$^+$)
IR$\nu$(Nujol)cm$^{-1}$: 3400, 3120, 1740, 1660

Examples 8–9

The corresponding starting compounds are treated in the same manner as described in Example 7 to give the following compounds.

(8) methyl 4-{[2-[(4-chlorophenyl)sulfonylamino]indan-5-yl]oxyacetylamino}butyrate; Yield: 86%
m.p. 114°–122° C. (recrystallized from isopropyl ethertetrahydrofuran)
MS(m/e): 480(M$^+$)
IR$\nu$(Nujol)cm$^{-1}$: 3390, 3130, 1740, 1660

(9) methyl 3-{[2-(phenylsulfonylamino)indan-5-yl]oxyacetylamino}propionate; Yield: 72%
m.p. 131°–133.5° C. (recrystallized from isopropyl ethertetrahydrofuran)
MS(m/e): 432(M$^+$)
IR$\nu$(Nujol)cm$^{-1}$: 3380, 3120–3200, 1730, 1650

Example 10

818 mg of methyl 3-{[2-[(4-chlorophenyl)sulfonylamino]indan-5-yl]oxyacetylamino}propionate are dissolved in 10 ml of methanol, and an aqueous In sodium hydroxide solution is added to the solution. The mixture is stirred at room temperature for 3 hours. The reaction mixture is evaporated to remove methanol and the residue is acidified with an aqueous 10% hydrochloric acid solution. The mixture is extracted with ethyl acetate. The extract is washed successively with an aqueous saturated sodium hydrochloride solution, dried and evaporated to remove solvent. The residue is recrystallized from a mixture of tetrahydrofuran and isopropyl ether to give 750 mg of 3-{[2-[(4-chlorophenyl)sulfonylamino]indan-5-yl]oxyacetylamino}propionic acid as colorless prisms. Yield: 92% m.p. 199°–201.5° C.
MS(m/e): 452(M$^+$)
IR$\nu$(Nujol)cm$^{-1}$: 3380, 3290, 1730, 1630
Sodium salt;
MS(m/e):475(M$^+$+Na)
IR$\nu$(Nujol)cm$^{-1}$: 3270(broad), 1660

Examples 11–12

The corresponding starting compounds are treated in the same manner as described in Example 10 to give the following compounds.

(11) 4-{[2-((4-chlorophenyl)sulfonylamino]indan-5-yl]oxyacetylamino}butyric acid; Yield: 83%
m.p. 168°–170.5° C. (recrystallized from tetrahydrofuranisopropyl ether-n-Hexane)
MS(m/e): 448(M$^+$-H$_2$O)
IR$\nu$(Nujol)cm$^{-1}$: 3390, 3290, 3170, 1700, 1660
Sodium salt;
MS(m/e):511(M$^+$+Na), 489(M$^+$+1)
IR$\nu$(Nujol)cm$^{-1}$: 3270, 1660

(12) 3-{[2-(phenylsulfonylamino)indan-5-yl]oxyacetylamino}propionic acid; Yield: 98%
m.p. 188°–191° C. (recrystallized from tetrahydrofuranisopropyl ether-n-hexane)
MS(m/e): 418(M$^+$)
IR$\nu$(Nujol)cm$^{-1}$: 3380, 3320, 3290, 1720, 1640
Sodium salt;
MS(m/e):463(M$^+$+Na), 441(M$^+$+1)
IR$\nu$(Nujol)cm$^{-1}$: 3270, 1660

(Preparation of the starting compounds)

Preparation (1) 64.1 g of powdered aluminum chloride are suspended in 170 ml of dichloromethane, and 33.9 g of chloroacetyl chloride are added dropwise to the suspension under ice-cooling and stirring. A solution of 35 g of 2-acethylaminoindan in 200 ml of dichloromethane are added dropwise to the mixture and the mixture is stirred at room temperature for 1 hour. Water is added to the reaction mixture in order to decompose excess amount of aluminum chloride. 30 ml of concentrated hydrochloric acid are added to the mixture and the mixture is evaporated to remove dichloromethane. The residue is extracted with tetrahydrofuran. The extract is washed successively with an aqueous saturated sodium bicarbonate solution and an aqueous saturated sodium chloride solution, dried and evaporated to remove solvent. The residue is recrystallized from isopropyl ether to give 47 g of 2-acetylamino-5-chloroacetylindan as colorless prisms. Yield: 93% m.p. 173°–174° C.

MS(m/e): 251(M+)

IR$\nu$(Nujol)cm$^{-1}$: 3280, 1690, 1640

(2) To a suspension of 5.03 g of 2-acetylamino-5-chloroacetylindan in chloroform are added 6.8 g of sodium dihydrogenphosphate and 10.06 g of m-chloroperbenzoic acid, and the mixture is refluxed for 5 hours under stirring. The reaction mixture is evaporated to remove solvent and the residue is extracted with ethyl acetate. The extract is washed successively with an aqueous sodium bicarbonate solution and an aqueous 10% hydrochloric acid solution, dried and evaporated to remove solvent. The residue is recrystallized from ethyl acetate-n-hexane-isopropyl ether to give 2.6 g of 2-acetylamino-5-chloroacetoxyindan. Yield: 48% m.p. 105.5°–107.5° C.

MS(m/e): 224(M+–COCH$_3$)

IR$\nu$(Nujol)cm$^{-1}$: 3280, 1770, 1630

(3) A mixture of 2.5 g of 2-acetylamino-5-chloroacetoxyindan, 50 ml of methanol and 46 ml of an aqueous 1N sodium hydroxide solution is stirred at room temperature for 2.5 hours. The reaction mixture is evaporated to remove methanol and the residual aqueous layer is washed with dimethyl ether, acidified and extracted with ethyl acetate. The extract is washed successively with an aqueous sodium bicarbonate solution and an aqueous sodium chloride solution, dried and evaporated to remove solvent. The residue is purified by silica gel column chromatography and recrystallized from isopropanol-isopropyl ether to give 1.01 g of 2-acetylamino-5-hydroxyindan as colorless needles. Yield: 61% m.p. 123°–126° C.

MS(m/e): 191(M+)

IR$\nu$(Nujol)cm$^{-1}$: 3300

(4) 1.05 g of 2-acetylamino-5-hydroxyindan are dissolved in 15 ml of acetone, and 1.14 g of powdered potassium carbonate and 1.01 g of methyl bromoacetate are added to the solution. The mixture is stirred overnight at room temperature and the reaction mixture is evaporated to remove solvent. The residue is extracted with ethyl acetate and the extract is washed successively with water and an aqueous sodium chloride solution, dried and evaporated to remove solvent. The residue is recrystallized from ethyl acetate-isopropyl ether-n-hexane to give 1.243 g of methyl (2-acetylaminoindan-5-yl)oxyacetate as colorless prisms. Yield: 86% m.p. 111°–114.5° C. (decomp.)

MS(m/e): 263(M+)

IR$\nu$(Nujol)cm$^{-1}$: 3300, 1770, 1640

(5) To 0.735 g of methyl (2-acetylaminoindan-5-yl)oxyacetate are added 6 ml of aqueous 10% hydrochloric acid solution, and the mixture is refluxed under stirring for 13 hours. The reaction mixture is evaporated to remove solvent and 10 ml of methanol are added to the residue. The mixture is refluxed for 1.5 hours and evaporated to remove methanol. The residue is recrystallized from methanol-diethyl ether to give 0.655 g of methyl (2-aminoindan-5-yl)oxyacetate hydrochloride as yellow prisms. Yield: 91% m.p. 156°–158.5° C.

MS(m/e): 221(M+, free base)

IR$\nu$(Nujol)cm$^{-1}$: 1760

What we claim is:

1. An indanoxyacetic acid derivative of the formula:

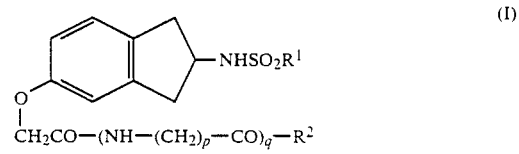

wherein $R^1$ is a phenyl group or a halogenophenyl group, $R^2$ is a hydroxy group or a $C_{1-6}$alkoxy group, p is an integer of 2 or 3 and q is an integer of 1, or a pharmaceutically acceptable salt thereof.

2. The compound as claimed in claim 1, wherein $R^1$ is a phenyl group or a chlorophenyl group and $R^2$ is a hydroxy group or a methoxy group.

3. The compound as claimed in claim 2, which is 3-{[2-(phenylsulfonylamino)indan-5yl]oxyacetylamino} propionic acid or a salt thereof.

4. The compound as claimed in claim 2, which is 3-{[2-[(4-chlorophenyl)sulfonylamino]indan-5-yl]oxyacetylamino}propionic acid or a salt thereof.

5. A pharmaceutical composition, exhibiting platelet aggregation inhibiting activity, which comprises a therapeutically effective amount of the compound as claimed in claim 1 and a pharmaceutically acceptable carrier therefor.

* * * * *